_United States Patent_ [19]

Lee et al.

[11] 3,976,777

[45] Aug. 24, 1976

[54] SALICYLAMIDES AND COMPOSITIONS THEREOF

[75] Inventors: Richard Martin Lee, Ickleford; George Sidney Sach, Welwyn, both of England

[73] Assignee: Smith Kline & French Laboratories, Inc., Welwyn Garden City, England

[22] Filed: July 16, 1975

[21] Appl. No.: 596,485

Related U.S. Application Data

[62] Division of Ser. No. 415,205, Nov. 12, 1973, Pat. No. 3,917,625.

[30] Foreign Application Priority Data

Dec. 6, 1972 United Kingdom............... 56234/72

[52] U.S. Cl. .................................. 424/263; 424/266
[51] Int. Cl.² ........................................ A61K 31/44
[58] Field of Search ..................................... 424/263

[56] References Cited
UNITED STATES PATENTS

| | | | |
|---|---|---|---|
| 2,554,186 | 5/1951 | Goldberg et al. ............ | 424/295 AM |
| 2,899,437 | 8/1959 | Shapiro et al. ............... | 260/295 AM |
| 3,270,026 | 8/1966 | Bercer et al. ................. | 260/295 AM |
| 3,276,289 | 4/1968 | Schmidt........................ | 260/295 AM |
| 3,406,168 | 10/1968 | Schmidt........................ | 260/295 AM |

OTHER PUBLICATIONS

Samejima, Chemical Abstracts, 55:10440d.
Profft, Chemical Abstracts, 60:4056f.
Jensen et al., Chemical Abstracts, 44:1454i.
May, Chemical Abstracts, 43:693b (1949).
Ioffe et al., Chemical Abstracts, 54:10938b, (1960).
Schraufstaetter et al., Chemical Abstracts, 56:4661g, (1962).

_Primary Examiner_—Norman A. Drezin
_Attorney, Agent, or Firm_—Joan S. Keps; Richard D. Foggio; William H. Edgerton

[57] ABSTRACT

3-tert.Butyl-5-nitro-N-pyrid-2′-yl salicylamides which have antiparasitic activity, compositions thereof and methods of controlling parasites in animals infected therewith.

6 Claims, No Drawings

SALICYLAMIDES AND COMPOSITIONS THEREOF

This is a division of application Ser. No. 415,205 filed Nov. 12, 1973, now U.S. Pat. No. 3,917,625.

The present invention relates to salicylamides and, in particular, to certain substituted 3-tert.butyl-5-nitro-N-pyrid-2'-yl salicylamides, to methods for their preparation and to compositions comprising these compounds. The compounds of the present invention possess activity against parasitic worms in particular against liver flukes in ruminant animals and thus the present invention also relates to methods of controlling these parasitic worms in animals by the administration to the animals of compositions comprising the salicylamides.

Throughout the present specification, by the terms "lower alkyl" and "lower alkoxy" we mean respectively an alkyl and an alkoxy group containing from 1 to 4 carbon atoms.

According to the present invention we provide compounds of the following formula I:

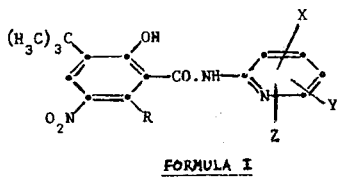

FORMULA I wherein R is hydrogen, or lower alkyl, preferably methyl; and X, Y and Z, which may be the same or different, are hydrogen, halogen, lower alkyl, lower alkoxy, nitro, cyano, sulphonamido or carbalkoxy; provided that X, Y and Z are not simultaneously all hydrogen.

The preferred compounds of Formula I which have particularly useful activity against parasitic worms are those wherein R is hydrogen or methyl; X is hydrogen, methyl, or halogen; Y is nitro or halogen and Z is hydrogen.

Specific preferred compounds are the following:
3-tert. butyl-5-nitro-6-methyl-N-(4'-methyl-5'-nitropyrid-2'-yl)salicylamide
3-tert. butyl-5-nitro-N-(5'-chloropyrid-2'-yl)salicylamide
3-tert. butyl-5-nitro-N-(5'-nitropyrid-2'-yl)salicylamide-
3-tert. butyl-5-nitro-N-(4'-methyl-5'-nitropyrid-2'-yl)salicylamide
3-tert. butyl-5-nitro-N-(5'-nitro-6'-methylpyrid-2'-yl)salicylamide
3-tert. butyl-5-nitro-N-(5'-iodopyrid-2'-yl)salicylamide
3-tert. butyl-5-nitro-N-(5'-bromopyrid-2'-yl)salicylamide
3-tert. butyl-5-nitro-N-(3',5'-dichloropyrid-2'-yl)salicylamide
3-tert. butyl-5-nitro-6-methyl-N-(5'-nitropyrid-2'-yl)salicylamide
3-tert. butyl-5-nitro-6-methyl-N-(5'-nitro-6'-methylpyrid-2'-yl) salicylamide
3-tert. butyl-5-nitro-6-methyl-N-(5'-chloropyrid-2'-yl)salicylamide
3-tert. butyl-5-nitro-6-methyl-N-(3',5'-dichloropyrid-2'-yl)salicylamide The compounds of the present invention may be prepared by processes which commence from a compound of the following Formula II:

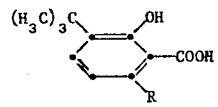

FORMULA II wherein R has the same significance as in Formula I.

In one such process, the compound of Formula II is first nitrated to produce the compound of Formula III wherein R has the same significance as in Formula I and G is hydrogen. Any suitable procedure may be used for this nitration reaction, for example it may be carried out using concentrated nitric acid in glacial acetic acid whilst controlling the temperature at about 10°–15°C.

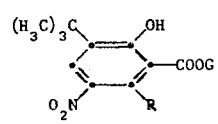

FORMULA III

The compounds of Formula I are then preferably prepared by the reaction of a reactive ester of Formula III wherein G is, for example, p-nitrophenyl with an amine of Formula IV at an elevated temperature e.g. in a high boiling solvent such as 1,2,4-trichlorobenzene or by fusion in the absence of any solvent,

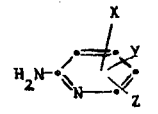

FORMULA IV wherein X, Y and Z have the same significance as in Formula I. The substance of Formula III wherein G is p-nitrophenyl may be prepared from the substance of that formula wherein G is hydrogen by reaction of the latter with thionyl chloride and then with p-nitrophenol. It will be obvious that the substance of Formula III wherein G is p-nitrophenyl may be prepared from the substance of Formula II by first forming the p-nitrophenyl ester of that substance and then nitrating. In the case of certain compounds it is possible to obtain the substance of Formula I by reacting the substance of Formula III wherein G is hydrogen directly with the amine of Formula IV in a suitable solvent such as benzene, chlorobenzene or toluene and in the presence of a halogenating condensation agent such as phosphorous trichloride.

The present invention also relates to anti-parasitic compositions comprising as the or an active ingredient an effective but non-toxic quantity of a compound of Formula I together with a pharmaceutically acceptable diluent or carrier. We also provide a method of controlling parasitic worms, in particular flukes, which comprises administering our anti-parasitic composition to a host animal such as a ruminant animal which is in need of such treatment. The composition is preferably given orally but, in certain cases, may be administered parenterally e.g. when the composition is in the form of a sterile micronised suspension or solution.

By an effective quantity of the compound of Formula I we mean a quantity which is active against parasites when given either for curative or prophylactic purposes to the animals concerned e.g. sheep or cattle. Our compounds are particularly active against Trematodes such as the flukes *Fasciola gigantica* and *Fasciola hepatica*. Generally effective and non-toxic doses are found to be in the range of from 1 to 40 mg./kg., preferably from 2 to 20 mg./kg. of bodyweight. The composition, in dosage unit form, may be administered to the animals from 1 to 5 times per day, but a single daily treatment is particularly convenient.

Veterinary compositions containing sufficient quantities of the compounds of Formula I to reach the dose levels mentioned above are prepared as known to the art by preparing tablets, capsules, boluses, liquid suspensions, powders, drenches or solutions for injection in packaged form. Alternatively, especially for prophylaxis, premix or feed compositions containing effective but non-toxic quantitites of the active salicylamide are used. For these purposes particulate carriers, inert powders or, especially, feed carriers such as soybean meal, corn oil, vermiculite, diatomaceous earth, barley or wheat are used. In dosage unit or premix feed compositions the compound can comprise from about 5 to 75% of the final composition as is convenient for the farmer or veterinarian. As an example, a 5% salicylamide vermiculite or soybean meal premix can be used which will be uniformly mixed with the animal feedstuff. Alternatively, a lick or pasture block can be used for field animals.

The activity of the compounds of Formula I against liver flukes in sheep was estimated by means of the following procedure.

Eggs of *Fasciola heptica* were collected from a suitable source, e.g. the bile of donor sheep or cattle. These eggs were embryonated and snails were infected (the genus *Lymnea* serves as intermediate host) to produce Metacercariae which are the infective forms for sheep. Each sheep in the test group was infected with 250 or more metacarcariae contained in a gelatin capsule which was administered orally and, when the infection became patent after 60 days, egg counts were carried out to determine the degree of worm burden. The test compound of Formula I was then administered and after a further 5 to 7 days a second egg count made from both treated and untreated sheep. Egg counts were repeated twice more after each of two more periods of 5 to 7 days. The livers of both treated and untreated sheep were also processed at the end of the experiment in order to recover and count *Fasciola hepatica*.

The results of these experiments using a number of compounds of Formula I are set out in the following table which shows the percentage reduction of *Fasciola hepatica* after administration of the compound in the dosage indicated. The minimum amount of compound producing only mild, transient overt symptoms of toxicity (Tolerance) is also shown in the table.

| Compound | Dosage mg/kg | % Reduction in F. Hepatica | Tolerance (mg/kg) |
|---|---|---|---|
| 3-tert. butyl-5-nitro-6-methyl-N-(4'-methyl-5'-nitropyrid-2'-yl)salicylamide | 2<br>5 | 90<br>100 | 30 |
| 3-tert. butyl-5-nitro-N-(5'-chloropyrid-2'-yl)salicylamide | 5<br>15 | 100<br>100 | 20 |
| 3-tert. butyl-5-nitro-N-(5'-nitropyrid-2'-yl)salicylamide | 2 | 100 | 2 |
| 3-tert. butyl-5-nitro-N-(4'-methyl-5'-nitropyrid-2'-yl) salicylamide | 15 | 100 | >20 |
| 3-tert. butyl-5-nitro-N-(5'-nitro-6'-methylpyrid-2'-yl) salicylamide | 10<br>15 | 100<br>100 | 15–20 |
| 3-tert. butyl-5-nitro-N-(5'-iodopyrid-2'-yl)salicylamide | 2<br>5<br>15 | 80<br>100<br>100 | 15–20 |
| 3-tert. butyl-5-nitro-N-(5'-brompyrid-2'-yl)salicylamide | 2<br>5<br>15 | 95<br>100<br>100 | 15–20 |
| 3-tert. butyl-5-nitro-N-(3',5'-dichloropyrid-2'-yl)salicylamide | 5<br>15 | <50<br>100 | 15–20 |
| 3-tert. butyl-5-nitro-6-methyl-N-(5'-nitropyrid-2'-yl) salicylamide | 2<br>5 | 100<br>100 | 5 |
| 3-tert. butyl-5-nitro-6-methyl-N-(5'-nitro-6'-methylpyrid-2'-yl) salicylamide | 10<br>15 | 100<br>100 | 15–20 |
| 3-tert. butyl-5-nitro-6-methyl-N-(5'-chloropyrid-2'-yl) salicylamide | 15 | 90 | >20 |
| 3-tert. butyl-5-nitro-6-methyl-N-(3',5'-dichlorpyrid-2'-yl) salicylamide | 5<br>15 | <50<br>100 | >40 |

The invention is illustrated but in no way limited by the following examples:

EXAMPLE I

Preparation of 3-tert. butyl-5-nitro-6-methyl-N-(4'-methyl-5'-nitropyrid-2'-yl)salicylamide i. 3-tert. Butyl-6-methyl salicylic acid (62.4 g 0.3M) was suspended in glacial acetic acid (300 ml) and cooled to 15°C. Concentrated nitric acid (22.5 ml) was added dropwise with stirring at such a rate that the temperature was maintained at approx. 10°–15°C. The mixture was stirred for 1 hour at this temp. and then poured onto crushed ice. A precipitate formed which was filtered off, washed with benzene and finally recrystallized from acetonitrile to give 3-tert. butyl-5-nitro-6-methyl salicylic acid (30.6 g) m.p. 225°–226°(-dec)

ii. The 3-tert. butyl salicylic acid (23.8 g 0.094M) was refluxed in thionyl chloride (150 ml) for 1 hour, the excess thionyl chloride removed by concentration at 15 mm and the final traces of thionyl chloride removed by reconcentration with dry benzene (80 mls). The residue was dissolved in benzene (150 mls), added to p-nitrophenol (13.5 g 0.097 mole) in benzene (150 mls) and the solution was refluxed for 4.5 hours. The benzene was removed by concentration under reduced pressure and the residual oil was crystallised from benzene/petroleum ether (1:2) and then recrystallised from water-ethanol to give p-nitrophenyl-3-tert. butyl-5-nitro-6-methyl salicylate (15 g) m.p. 131°–133°C.

iii. p-Nitrophenyl-3-tert butyl-5-nitro-6-methyl salicylate (10.2 g 0.027M) and 2-amino-4-methyl-5-nitropyridine (4.15 g, 0.027M) was heated at 180°C for 1 hour under a nitrogen atmosphere. The reaction mixture was then stirred with 50 ml anhydrous diethylether, filtered and the product was crystallised from ethanol-water to give 3-tert butyl-5-nitro-6-methyl-N-(4'-methyl-5'-nitropyrid-2'-yl)salicylamide (6.1 g), m.p. 207°–208°C (dec.). [Found: C, 55.6; H, 5.2; N, 14.4%. $C_{18}H_{20}N_4O_6$ requires: C, 55.7; H, 5.2; N, 14.4%].

EXAMPLE 2

Preparation of 3-tert. butyl-5-nitro-6-methyl-N-(5'-nitropyrid-2'-yl) salicylamide 3-tert. Butyl-5-nitro-6-methyl salicylic acid (3.4 g 0.013M), 2-amino-5nitropyridine (3.4 g 0.024M) and phosphorous trichloride (0.46 ml 0.005M) were added to 16 ml chlorobenzene, refluxed for 3 hours and evaporated to dryness. The residue was treated with acetone, the soluble portion evaporated, dissolved in dichloromethane, extracted with 2N hydrochloric acid and then chromatographed using a silica column. The resultant crude product was treated in turn with 10% sodium bicarbonate solution, 2N hydrochloric acid and finally water. It was then recrystallised from ethanol to give 3-tert. butyl-5nitro-6-methyl-N-(5'-nitropyrid-2'-yl)salicylamide (1.1 g), m.p. 186.5°–189°C. [Found: C, 54.6; H, 5.0; N, 14.7%, $C_{17}H_{18}N_4O_6$ requires: C, 54.5; H, 4.9; N, 15.0%].

EXAMPLE 3

Preparation of 3-tert. butyl-5-nitro-6-methyl-N-(5'-nitro-6-methylpyrid-2'-yl)salicylamide p-Nitrophenyl-3-tert. butyl-5-nitro-6-methylsalicylate (3.74 g 0.01M) and 2-amino-5-nitro-6methylpyridine (1.53 g 0.01M) were fused together for an hour at 180°C and then allowed to cool. The resultant solid mass was chromatographed on a column of silica using dichloromethane as eluent. The crude product was recrystallised from petroleum ether (b.p. 100°–120°) to give 3-tert. butyl-5-nitro-6-methyl-N-(5'-nitro-6'-methylpyrid-2'-yl)salicylamide (2.85 g), m.p. 164.5-165.5°C. [Found: C, 55.8; H, 5.3; N, 14.4%. $C_{18}H_{20}N_4O_6$ requires: C. 55.7; H, 5.2; N, 14.4%].

EXAMPLE 4

Preparation of 3-tert. butyl-5-nitro-6-methyl-N-(5'-chloropyrid-2'-yl)salicylamide A mixture of p-nitrophenyl-3-tert. butyl-5-nitro-6-methyl salicylate (7.46 g 0.02M) and 2-amino-5-chloropyridine (2.56 g 0.02M) was fused at 180°C under nitrogen for 50 minutes. The cooled product was triturated with diethyl ether to give a solid which was twice recrystallised from ethanol to give 3-tert. butyl-5-nitro-6-methyl-N-(5'-chloropyrid-2'-yl) salicylamide (2.0 g), m.p. 206.5–207.5°C. [Found: C, 56.3; H, 5.0; N, 11.5; Cl, 10.0%. $C_{17}H_{18}Cl\ N_3O_4$ requires: C, 56.1; H, 5.0; N, 11.6; Q, 9.8%].

EXAMPLE 5

Preparation of 3-tert. butyl-5-nitro-6-methyl-N-(3',5'-dichlorpyrid-2'-yl)salicylamide 3-tert. Butyl-5-nitro-6-methyl salicylic acid (4.2 g 0.017M). 2-amino-3,5-dichloropyridine (5.45 g 0.03M) and phosphorous trichloride (0.57 ml 0.007M) were added to chlorobenzene (20 ml), refluxed for 3 hours and then evaporated to dryness. The red residue was extracted with diethyl ether and the ether extract extracted with 2N hydrochloric acid. After drying, the ethereal solution was evaporated to dryness and the residue chromatographed on a silica column using dichloromethane as eluent. The crude product was twice recrystallised from ether/petroleum ether (b.p. 60°–80°) to yield 3-tert. butyl-5-nitro-6-methyl-N-(3',-5'-dichloropyrid-2'-yl) salicylamide (1.85 g), m.p. 168.5°–169.5°C. [Found: C, 51.3; H, 4.4; N, 10.9; Cl 18.0%. $C_{17}H_{17}Cl_2N_3O_4$ requires: C, 51.3; H, 4.3; N, 10.6; Cl, 17.8%.]

EXAMPLE 6

Preparation of 3-tert. butyl-5-nitro-N-(5'-nitropyrid-2'-yl)salicylamide i. 3-tert. Butyl-5-nitrosalicylic acid (5.0g 0.021M) was refluxed for an hour with thionyl chloride (40 ml), the excess thionyl chloride then removed by distillation and the residue twice distilled to dryness with dry benzene (20 ml) under reduced pressure. The residue was dissolved in dry benzene (20 ml) and added to a suspension of p-nitrophenol (3.0 g 0.022M) in dry benzene (30 ml). The mixture was refluxed for 3 hours, filtered and the filtrate concentrated to a brown oil, which crystallised. Recrystallisation from benzene/petroleum ether (b.p. 60°–80°) and then from acetonitrile/water yielded p-nitrophenyl-3-tert. butyl-5-nitrosalicylate as pale yellow needles (2.0 g), m.p. 150°–152°C. [Found: C, 56.6; H, 4.5; N, 7.8% $C_{17}H_{16}N_2O_7$ requires: C, 56.7; H, 4.5; N, 7.8%].

ii. p-Nitrophenyl-3-tert. butyl-5-nitrosalicylate (5.0 g 0.014M) and 2-amino-5-nitropyridine (1.9 g 0.014M) were dissolved in 1,2,4-trichlorobenzene and heated for an hour at 190°C. The solvent was removed by vacuum distillation and the residue extracted with diethyl ether. Evaporation of the ethereal extract and recrystallisation of the residue twice from methanol yielded 3-tert. butyl-5-nitro-N-(5'-nitropyrid-2'-yl) salicylamide (1.55 g), m.p. 209°–210°C. [Found: C, 53.1; H, 4.5; N, 15.2%. $C_{16}H_{16}N_4O_6$ requires: C, 53.3; H, 4.5; N, 15.6%.]

EXAMPLE 7

Preparation of 3-tert. butyl-5-nitro-N-(4'-methyl-5'-nitropyrid-2'-yl) salicylamide i. 3-tert. Butyl-salicylic acid (22 g 0.11M) was refluxed with thionyl chloride (100 ml) for 20 minutes, the excess thionyl chloride was then removed and the residue was dissolved in benzene. p-Nitrophenol (15.8 g 0.11M) was added and the solution was refluxed for 5 hours, after which time the benzene was removed to yield a dark oil. This oil was dissolved in diethyl ether and, after extraction with 10% sodium bicarbonate solution, the ethereal solution was evaporated and the residue was crystallised from petroleum ether (B.pt. 60/80) to give p-nitrophenyl-3-tert. butyl-salicylate (32.9 g), m.p. 89.5°–90.5°C.

ii. p-Nitrophenyl-3-tert. butyl-salicylate (32.9 g 0.10M) was dissolved in glacial acetic acid and concentrated nitric acid (33 ml) was added dropwise, the temperature being maintained below 40°C throughout the addition. The temperature was then reduced to 10°C for 30 minutes, the solution poured onto crushed ice and the precipitated product filtered off. Recrystallisation from petroleum ether (b.p. 60°–80°) gave pure p-nitrophenyl-3-tert. butyl-5-nitrosalicylate (26.0 g) m.p. 150°–151°C.

iii. p-Nitrophenyl-3-tert. butyl-5-nitrosalicylate (2.8 g 0.008M) and 2-amino-4-methyl-5-nitropyridine (1.2 g 0.008M) were heated at 180°C for an hour under a nitrogen atmosphere. Ethanol (20 ml) and a few drops of water were added and vigorous stirring resulted in a crystalline product which was chromotographed on a silica column using dichloromethane as eluent. The product was crystallised from aqueous ethanol to give 3-tert. butyl-5-nitro-N-(4'-methyl-5'-nitropyrid-2'-yl) salicylamide (1.9 g), m.p. 172°–173°C (dec.). [Found: C, 54.8; H, 4.8; N, 15.0%. $C_{17}H_{18}N_4O_6$ requires: C, 54.5; H, 4.9; N, 15.0%.]

EXAMPLE 8

Preparation of 3-tert. butyl-5-nitro-N-(5'-nitro-6'-methylpyrid-2'-yl) salicylamide A mixture of p-nitrophenyl-3-tert. butyl-5-nitrosalicylate (7.26 g 0.02M) and 2-amino-5-nitro-6-methylpyridine (3.0 g 0.022M) was heated for 40 minutes at 180°C and, after cooling, was allowed to stand under diethyl ether for 16 hours. The product was filtered off and recrystallised three times from dioxan/ethanol to yield 3-tert. butyl-5-nitro-N-(5'-nitro-6'-methylpyrid-2'-yl) salicylamide (3.0 g), m.p. 197°–198°C. [Found: C, 54.4; H, 4.9; N, 14.8% $C_{17}H_{18}N_4O_6$ requires: C, 54.5; H, 4.9; N, 15.0%.]

EXAMPLE 9

Preparation of 3-tert. butyl-5-nitro-N-(5'-iodopyrid-2'-yl) salicylamide

A mixture of p-nitrophenyl-3-tert. butyl-5-nitrosalicylate (7.7 g 0.021M) and 2-amino-5-iodopyridine (4.7 g 0.021M) was heated at 180°C for 40 minutes. The product was cooled, triturated with diethyl ether and the filtered-off residue recrystallised from dioxan/ethanol three times to yield 3-tert. butyl-5-nitro-N-(5'-iodopyrid-2'-yl) salicylamide (3.38 g), m.p. 214°–215°C. [Found: C, 43.3; H, 3.8; N, 9.4; I, 29.0%. $C_{16}H_{16}IN_3O_4$ requires: C, 43.6; H, 3.7; N, 9.5; I 28.8%.]

EXAMPLE 10

Preparation of 3-tert. butyl-5-nitro-N-(5'-bromopyrid-2'-yl) salicylamide p-Nitrophenyl-3-tert. butyl-5-nitrosalicylate (5.5 g 0.015M) and 2-amino-5-bromopyridine (1.88 g 0.015M) were fused at 180°C for 40 minutes and then allowed to cool. The resultant solid was extracted into ether. the ethereal solution evaporated to dryness and the residue recrystallised twice from chloroform/petroleum ether to yield 3-tert butyl-5-nitro-N-(5'-bromopyrid-2'-yl) salicylamide (2.75 g), m.p. 197°–198°C. [Found: C, 48.9; H, 4.2; N, 10.7; Br, 19.8%. $C_{16}H_{16}BrN_3O_4$ requires: C, 48.8; H, 4.1; N, 10.7; Br, 20.3%.]

EXAMPLE 11

Preparation of 3-tert. butyl-5-nitro-N-(5'-chloropyrid-2'yl) salicylamide p-Nitrophenyl-3tert. butyl-5-nitrosalicylate (7.7 g 0.021M), 2-amino-5-chloropyridine (2.45 g 0.021M) and 1,2,4-trichlorobenzene (10 ml) were heated for 40 minutes at 180°C and the resultant solution, after cooling, was poured into petroleum ether (b.p. 40°–60°) (250 ml). The crude product was dissolved in dichloromethane and chromatographed on a silica column, the eluent being evaporated to dryness and the residue twice recrystallised from dichloromethane to yield 3-tert. butyl-5-nitro-N-(5'-chloropyrid-2'-yl) salicylamide (2.6 g), m.p. 201.5°–202.5°C. [Found: C, 54.7; H, 4.8; N, 12.1%. $C_{16}H_{16}ClN_3O_4$ requires: C, 55.0; H, 4.6; N, 12.0%.]

EXAMPLE 12

Preparation of 3-tert. butyl-5-nitro-N-(3',5'-dichloropyrid-2'-yl) salicylamide p-Nitrophenyl-3tert. butyl-5-nitrosalicylate (2.2 g 0.06M) and 2-amino-3',5'-dichloropyridine (1.1g 0.06M) were fused together for 40 minutes at 180°C and then cooled to yield a solid which was stirred first with water (70 ml) containing dilute hydrochloric acid (2 ml) and then with methanol (40 ml). The crude product was filtered off, dried and recrystallised twice from ether/petroleum ether (b.p. 60°–80°) (1:2) to yield 3-tert. butyl-5-nitro-N-(3',5'-dichloropyrid-2'-yl) salicylamide (1.3 g), m.p. 178°–179°C. [Found: C, 49.8; H, 4.1; N, 10.9; Cl, 18.4% $C_{16}H_{15}N_3Cl_2O_4$ requires: C, 50.0; H, 3.9; N, 10.9; Cl, 18.5%.]

EXAMPLE 13

The reaction of p-nitrophenyl-3-tert. butyl-5-nitro-6-methyl salicylate in the process of Example I (iii) with the following 2-aminopyridines:
 a. 2-amino-5-cyanopyridine
 b. 2-amino-5-carboethoxypyridine
 c. 2-amino-5-methoxypyridine
 d. 2-amino-5-sulphonamidopyridine
 e. 2-amino-3,5,6-trifluoropyridine yields the following products:
 a. 3-tert.butyl-5-nitro-6-methyl-N-(5'cyanopyrid-2'-yl) salicylamide
 b. 3-tert.buty-5-nitro-6-methyl-N-(5'-carboethoxypyrid-2'-yl) salicylamide
 c. 3-tert.butyl-5-nitro-6-methyl-N-(5'-methoxypyrid-2'-yl) salicylamide
 d. 3-tert.butyl 5 -nitro-6-methyl-N-(5'-sulphonamidopyrid-2'-yl) salicylamide
 e. 3-tert.butyl-5-nitro-6-methyl-N-(3',5',6'-trifluoropyrid-2'-yl) salicylamide

EXAMPLE 14

A veterinary composition was prepared in the form of a sheep drench from the following ingredients:

| | Parts by weight |
|---|---|
| 3-tert. Butyl-5-nitro-6-methyl-N-(4'-methyl-5'-nitropyrid-2'-yl) salicylamide | 20 |
| Terra alba | 75.5 |
| Tragacanth | 3.0 |
| Sodium lauryl sulphate | 1.5 |

These ingredients were mixed to give a water-dispersible powder to be used orally as necessary and practical to control infections. For example, a suitable oral dosing drench can be made from 5 g of the powder and 5 ml of water.

EXAMPLE 15

A ruminant bolus may be prepared from the following ingredients:

| | Parts by weight |
|---|---|
| 3-tert. Butyl-5-nitro-6-methyl-N-(4'-methyl-5'-nitropyrid-2'-yl) salicylamide | 5.0 |
| Calcium phosphate | 40.0 |
| Maize starch | 5.4 |
| Talcum | 1.4 |
| Gum arabic | 1.5 |

-continued

| | Parts by weight |
|---|---|
| Magnesium stearate | 0.5 |

The salicylamide and phosphate are first mixed and screened and then granulated, using half of the starch. The resultant screened and dried granules are mixed with the remaining ingredients, blended thoroughly and compressed on a bolus press. Each bolus weighs approximately 5.4 grams.

We claim:

1. A veterinary composition for anti-parasitic use comprising an acceptable diluent or carrier and as an active ingredient an effective but nontoxic quantity of a salicylamide compound of the formula:

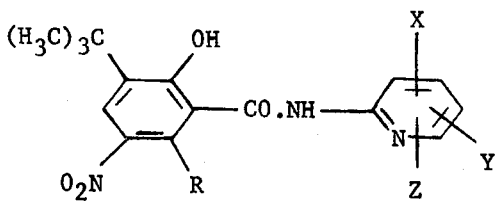

wherein R is hydrogen or lower alkyl; and X, Y and Z, which may be the same or different, are hydrogen, halogen, lower alkyl, lower alkoxy, nitro, or carbalkoxy; provided that X, Y and Z are not simultaneously all hydrogen.

2. The composition of claim 1 wherein R is hydrogen or methyl; X is hydrogen, methyl or halogen; Y is nitro or halogen and Z is hydrogen.

3. The composition of claim 1 in which the salicylamide compound is 3-tert.butyl-5-nitro-6-methyl-N-(4'-methyl-5'-nitropyrid-2'-yl) salicylamide.

4. A method of controlling parasitic worms in a ruminant animal in need thereof which comprises administering to said animal an effective amount of a composition of claim 1.

5. The method of claim 4 wherein R is hydrogen or methyl; X is hydrogen, methyl or halogen; Y is nitro or halogen and Z is hydrogen.

6. The method of claim 4 in which the salicylamide compound is 3-tert.butyl-5-nitro-6-methyl-N-(4'-methyl-5'-nitropyrid-2'-yl) salicylamide.

* * * * *

UNITED STATES PATENT AND TRADEMARK OFFICE
CERTIFICATE OF CORRECTION

PATENT NO. : 3,976,777
DATED : August 24, 1976
INVENTOR(S) : Richard Martin Lee and George Sidney Sach It is certified that error appears in the above-identified patent and that said Letters Patent are hereby corrected as shown below:

On the first page of the patent, in the left-hand column, item [73] should read:

[73] Assignee: Smith Kline & French Laboratories Limited, Welwyn Garden City, England Column 3, line 43, "60" should read -- 80 -- .

Column 8, line 35, "buty-" should read -- butyl- -- .

*Signed and Sealed this*

Sixteenth Day of November 1976

[SEAL]

*Attest:*

RUTH C. MASON
*Attesting Officer*

C. MARSHALL DANN
*Commissioner of Patents and Trademarks*